United States Patent [19]
Lekholm et al.

[11] Patent Number: 4,776,338
[45] Date of Patent: Oct. 11, 1988

[54] CARDIAC PACER FOR PACING A HUMAN HEART AND PACING METHOD

[75] Inventors: Anders Lekholm; David Amundson, both of Bromma, Sweden

[73] Assignee: Siemens Aktiengesellschaft, Berlin and Munich, Fed. Rep. of Germany

[21] Appl. No.: 874,596

[22] Filed: Jun. 16, 1986

[51] Int. Cl.$^4$ .............................. A61N 1/36
[52] U.S. Cl. .............................. 128/419 PG
[58] Field of Search .............................. 128/419 PG

[56] References Cited

U.S. PATENT DOCUMENTS

| | | | |
|---|---|---|---|
| 3,311,111 | 3/1967 | Bowers | 128/419 PG |
| 3,596,718 | 8/1971 | Krusner et al. | 128/419 PG |
| 3,833,005 | 9/1974 | Wingrove | 128/419 PG |
| 3,921,642 | 11/1975 | Preston et al. | 128/419 PG |
| 4,038,991 | 8/1977 | Walters | 128/419 PG |
| 4,108,148 | 8/1978 | Cannon, III | 128/419 PG |
| 4,114,628 | 9/1978 | Rizk | 128/419 PG |
| 4,298,007 | 11/1981 | Wright et al. | 128/419 PG |
| 4,399,820 | 8/1983 | Wrrtzfeld | 128/419 PG |
| 4,576,183 | 3/1986 | Plicchi et al. | 128/419 PG |

FOREIGN PATENT DOCUMENTS

| | | | |
|---|---|---|---|
| 0089014 | 9/1983 | European Pat. Off. | 128/419 PG |
| 0140472 | 5/1985 | European Pat. Off. | 128/419 PG |
| 2109073 | 5/1972 | France | 128/419 PG |

Primary Examiner—William E. Kamm
Assistant Examiner—Timothy J. Keegan
Attorney, Agent, or Firm—Hill, Van Santen, Steadman & Simpson

[57] ABSTRACT

A cardiac pacer, which generates pacing pulses at a predetermined basic pacing rate, includes a device for sensing physical activity and for generating a control signal dependent thereon, a device for varying the predetermined basic pacing rate independent on the control signal and a device for forcing the pacing rate back to a lower rate if the pacing rate runs at or above a predetermined high rate for a predetermined time period.

17 Claims, 2 Drawing Sheets

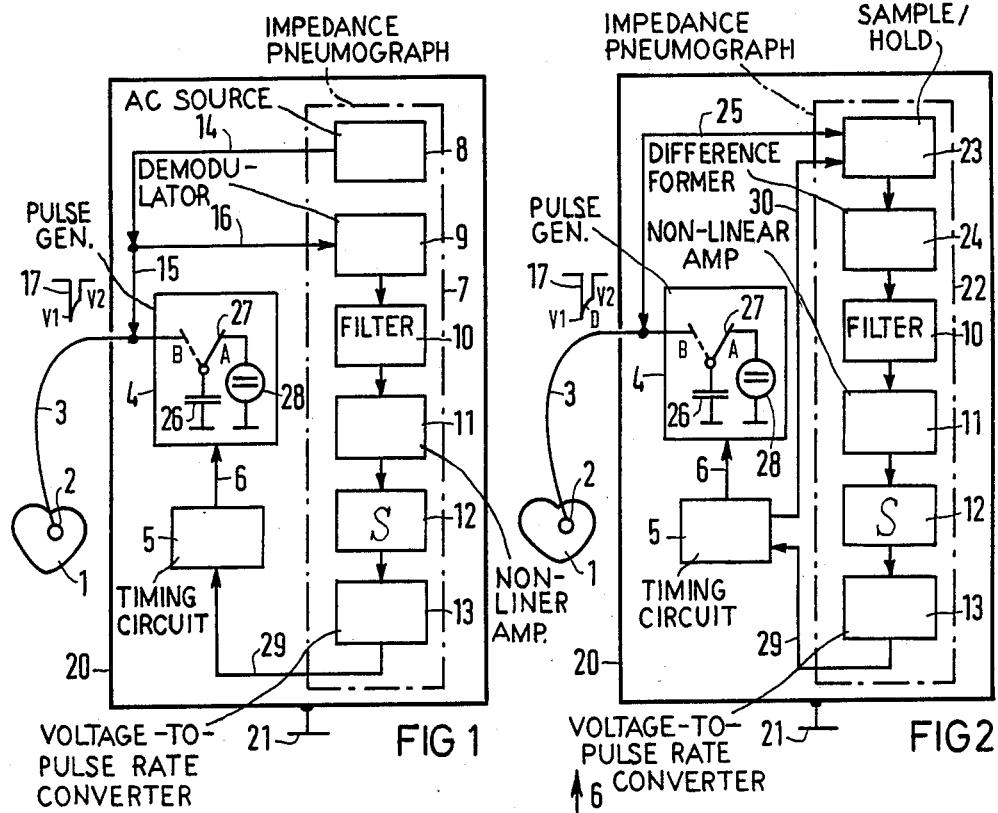
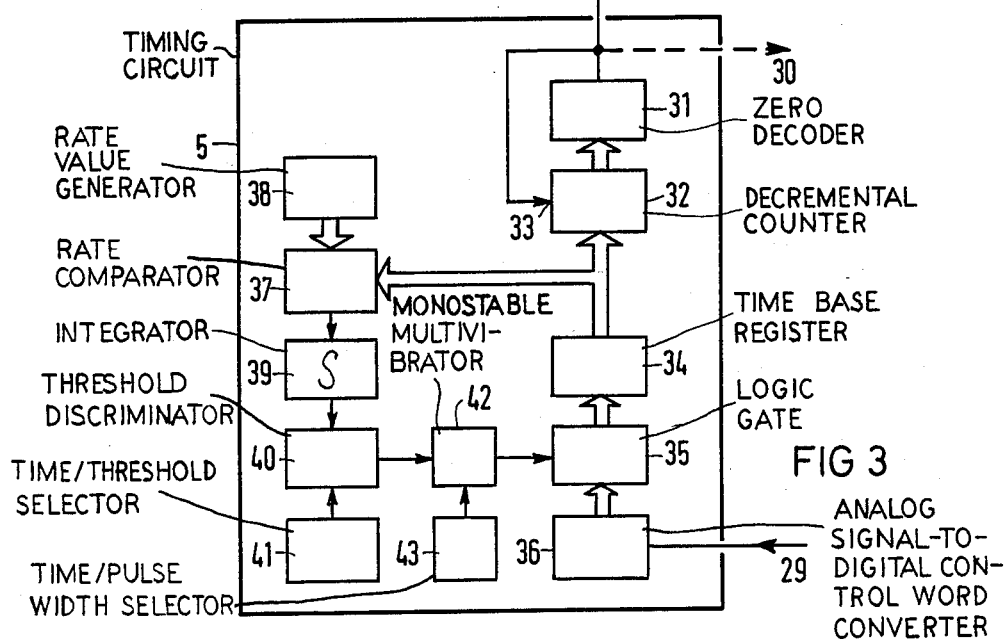

CARDIAC PACER FOR PACING A HUMAN HEART AND PACING METHOD

BACKGROUND OF THE INVENTION

Field of the Invention

The invention relates to a cardiac pacer for pacing a heart, in particular a human heart, wherein the pacing rate is controlled by a signal that is dependent upon physical activity or a measured physiological change in the body of a patient.

Related Applications

The subject matter of this application is related to the following co-pending applications filed simultaneously herewith: "Cardiac Pacer For Pacing A Human Heart," Elmqvist, Ser. No. 874,588; "A Cardiac Pacer For Pacing A Heart," Elmqvist, Lekholm, Hedberg and Amundson, Ser. No. 874,597; " "A Cardiac Pacer For Pacing A Human Heart," Lekholm and Amundson, Ser. No. 874,591; and "A Cardiac Pacer For Pacing A Heart," Lekholm and Amundson, Ser. No. 874,585; and "A Cardiac Pacer For Pacing A Human Heart," Amundson, Ser. No. 874,588.

Description of the Prior Art

Conventional cardiac pacers of this kind, in particular of the respiration rate responsive type, are for example described in the U.S. Pat. No. 3,593,718 and in the European patent application No. 0,089,014.

The conventional cardiac pacers can suffer from erroneous rate increases either due to instability or drift in the sensor itself or due to sensing of interference or due to a poor coupling between the sensed variable and the corresponding physiological need for cardiac output. As many of the elderly patients in whom rate-responsive pacemaker systems are implanted have low tolerance for the strain of a prolonged elevated heart rate, these conditions represent a potential hazard to the patient.

SUMMARY OF THE INVENTION

Objects

It is an object of this invention to provide for an improved cardiac pacer which is safe from hazardous erroneous rate increases.

Summary

According to this invention an improved cardiac pacer is provided which comprises
  (a) means for generating pacing pulses at a predetermined basic pacing rate;
  (b) means for transmitting the pacing pulses to the heart for pacing;
  (c) means for sensing physical activity and for generating a control signal dependent thereon;
  (d) means for varying the predetermined basic pacing rate dependent on the control signal; and
  (e) means for forcing the pacing rate back to a lower rate if the pacing rate runs at or above a predetermined high rate for a predetermined time period.

The foregoing and other objects, features and advantages of the invention will be apparent from the following more particular description of a preferred embodiment of the invention, as illustrated in the accompanying drawings.

BRIEF DESCRIPTION OF THE DRAWINGS

FIG. 1 shows a first embodiment of a cardiac pacer comprising the invention in a schematic block diagram.

FIG. 2 shows a second embodiment of a cardiac pacer comprising the invention in a schematic block diagram: and FIG. 3 shows the time base unit of the embodiment of FIGS. 1 and 2 in more detail.

DESCRIPTION OF THE PREFERRED EMBODIMENT

Figure 4:
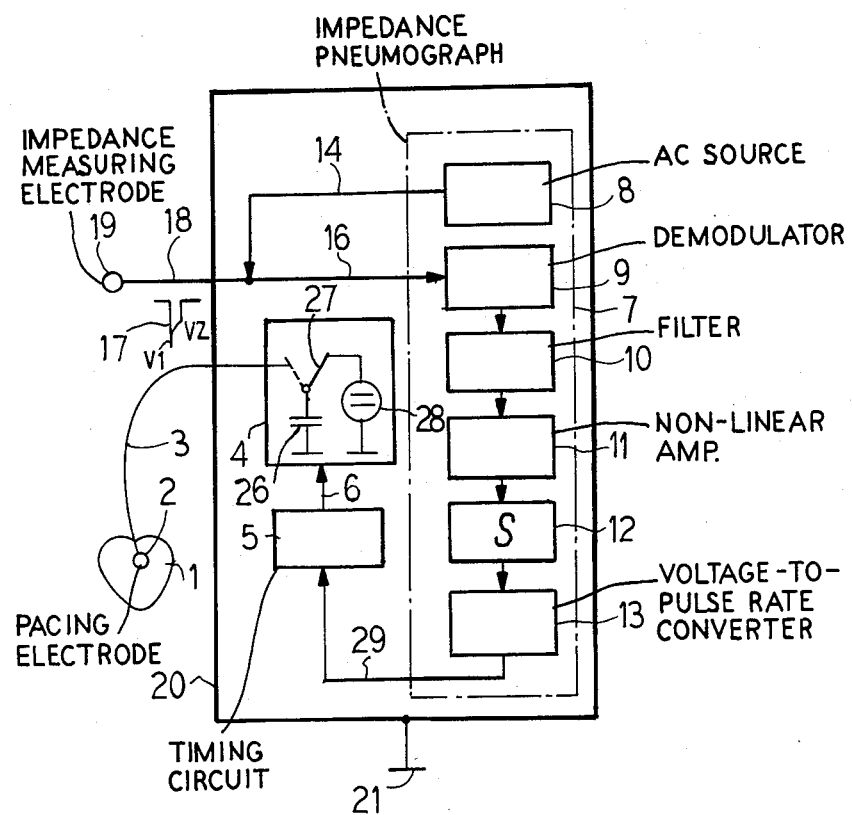
FIG. 4 shows another embodiment of a cardiac pacer comprising the invention in a schematic block diagram having an impedance measuring electrode.

In FIGS. 1 and 2 a human heart which has to be paced is generally designated with 1. A pacing electrode 2 is inserted in the human heart 1 in a manner and position such that the heart can most efficiently be paced. The pacing electrode 2 is connected through a pacing lead 3 with a pacing pulse generator 4. A timing circuit 5 controls the pacing rate of the pacing pulse generator 4 through line 6.

According to FIG. 1 an impedance pneumograph (also called a pneumatograph) 7 comprises an AC source 8 generating a continuous alternating current, a demodulator 9, a filter 10, a non-linear amplification circuitry 11, an integrator 12, and a voltage to pulse rate converter 13.

The AC source 8 is connected with the pacing lead 3 through leads 14, 15. The demodulator 9 is connected with the pacing lead 3 through leads 15, 16. Under the circumstances the current of the AC source 8 is supplied to the pacing electrode 2 together with the pacing pulses 17. This embodiment can be modified as shown in FIG. 4 wherein a separate electrode is provided for impedance measurement. In this case the AC source 8 and the demodulator 9 are disconnected from pacing lead 3 and instead are connected through additional lead 18 with the separate impedance measuring electrode 19. In both cases the output signal of the demodulator 9 is a measure for the breathing rate, i.e. a respiratory signal.

In FIG. 1 the pacing pulse generator 4, the timing circuit 5 and the impedance pneumograph 7 are all encapsuled in an implantable conductive (metallic) housing 20 which is the housing of the cardiac pacer. The conductive housing 20 defines both the indifferent electrode for pacing and the second electrode for impedance measurement as indicated in FIG. 1 with reference numeral 21.

As illustrated in FIGS. 1 and 2 the pacing pulse generator 4 comprises an output capacitor 26 which is switchable by means of switch 27 between battery 28 (switch position A) and pacing lead 3 (switch position B). In switch position A the output capacitor 26 is charged by the battery 28 to a voltage V1. In switch position B the output capacitor 26 is discharged through pacing lead 3 as pacing pulse 17.

In the embodiment of FIG. 2 the amount of discharge depends on the impedance variations of the patient's thorax during respiration. According to FIG. 2 the pacing pulse 17 discharges from V1 to V2 (amplitude decay D). The sample and hold circuitry 23 samples and holds the voltages V1, V2 of output capacitor 26. The difference former 24 forms the difference V1−V2 which is again a measure for the breathing rate, i.e. a respiratory signal.

In both embodiments of FIGS. 1 and 2 the non-linear amplification circuitry 11 amplifies the filtered respiratory signal such that signal portions having higher amplitudes are more amplified than signal portions having lower amplitudes. Under the circumstances signal portions of interest including the respiration signal, are enhanced with respect to low amplitude noise for further processing. Non-linear amplification circuits of this kind are well known in the art and need not be described in more detail. The output signal of the non-linear amplification circuitry 11 is integrated in integrator 12 over a period of time, e.g. in the range of 5 to 30 s. By integrating high-frequency noise is significantly reduced. The voltage to pulse rate converter 13 in FIGS. 1 and 2 converts the integrated signal into a pulse rate according to the breathing rate.

The voltage to pulse rate converter 13 controls the timing circuit 5 through line 29 such that a predetermined (e.g. programmable) basic pacing rate of the pacing pulse generator 4 is varied dependent on the respiratory signal. In FIG. 2 the line 30 is a control line from the time base unit 5 to the sample and hold circuitry 23 of impedance pneumograph 22.

According to this invention and as depicted in more detail in FIG. 3 the timing circuit 5 comprises a zero decoder 31, a decremented counter 32 having a reset input 33, a time base register 34, a logic gate 35, an analog signal to digital control word converter 36, a high rate comparator 37 for the output of the time base register 34 and a predetermined high rate value, e.g. 120 beats/min. of a high rate value generator 38, an integrator 39, a threshold discriminator 40, a time/threshold selector 41 connected with the threshold discriminator 40, a monostable multivibrator 42 and a time/pulse width selector 43 connected with the monostable multivibrator 42.

The analog signal to digital control word converter 36 converts the analog pulse rate signal of the voltage to pulse rate converter 13 into a digital control word. This digital control words is supplied through open gate 35 to the time base register 34. It controls the time base register 34 such that a basic pacing rate, e.g. 60 beats/min., is varied dependent on the respiration rate. When the breathing rate increases the time base register 34 increases the counting speed of the decremental counter 32 so that it reaches zero faster than at basic rate. Under the these conditions the zero decoder 31 generates switching signals at higher rates, so that the output capacitor 26 of the pacing pulse generator 4 charges and discharges at higher rates. As a result the pacing rate increases dependent on increasing breathing rate as desired.

However, as soon as the output of the time base register 34 reaches (and as long as it is running at or above) the predetermined high rate value of the high rate value generator 38, the high rate comparator 37 generates an output signal, e.g. a DC signal, which is integrated by integrator 39. After a certain time period, which is preselectable by means of time/threshold selector 41 through preselecting at a predetermined threshold at threshold discriminator 40, the output signal of integrator 39 exceeds the preselected threshold of the threshold discriminator 40. The threshold discriminator 40 in response triggers a monostable multivibrator 42 which generates an output pulse the width of which is programmable by means of time/pulse width selector 43. this output pulse of monostable multivibrator 42 continues until the end of the output pulse.

As a result the time base register 34 is disconnected from the output of the analog signal to digital control word converter 36. The time base register 34 switches back to basic pacing rate, e.g. 60 beats/min.

Under the circumstances this invention safeguards a patient, in particular elderly patient, against the strain of a prolonged elevated heart rate. If the pacer runs for a predetermined time at or above a predetermined high rate, then it will react as if the control signal which is dependent upon physical activity (here the respiration signal) disappeared so that the pacer automatically returns to its basic pacing rate. The time during which the pacer will run at basic rate after a forced return to basic rate is programmable. An additional criterion which may be used is that the control signal sensor input must return below the predetermined high rate to a lower value before the pacer starts tracking the control signal again.

A similar function has already been described, adding a slow time constant to the detector response so that a constant detector output will be regarded as a detector output that slowly returns to the resting, non-active state. The latter method has the disadvantage relative to this invention in the sense that it limits the exercise capacity of the patient for any activity that is longer than the time constant, which typically would be of the order of minutes or possibly up to one hour.

With the method described in this invention the heart rate may be elevated for may hours during normal physical activity. The rate limitation is only activated when the pacer stays at the high rate for the prolonged period of time.

Another variation of the invention allows for the forced return at a predetermined rate between the basic rate and the high rate of the pacemaker.

Having thus described the invention with particular references to the preferred forms thereof, it will be obvious to those skilled in the art to which the invention pertains, after understanding the invention, that various changes and modifications may be made therein without departing from the spirit and scope of the invention as defined by the claims appended hereto. For example the impedance measurement electrodes do not need to be implanted. They can also be secured on the patient's chest, if desired. Such a possibility is for example illustrated in U.S. Pat. No. 3,593,718. Also, instead of a respiratory signal any other signal of physiologic need for increased cardiac output, e.g. temperature, $pO_2$ signal etc., may be employed to control the rate of the pacer.

What is claimed is:

1. A cardiac pacer for pacing a heat in a patient comprising
   (a) means for generating pacing pulses at a predetermined pacing rate;
   (b) means for transmitting the pacing pulses to the heart for pacing;
   (c) means for sensing physical activity of said patient and for generating a control signal dependent thereon;
   (d) means for varying the predetermined basic pacing rate dependent on the control signal;
   (e) means for monitoring when the pacing rate runs at least at a predetermined high rate for a predetermined time period and for generating an output signal if said high rate is reached; and
   (f) means for forcing said pacing rate back to a lower rate dependent on said output signal.

2. A cardiac pacer as claimed in claim 1, wherein said means for forcing forces said pacing rate back to the predetermined basic pacing rate.

3. A cardiac pacer as claimed in claim 2, further comprising means for controlling said means for generating pacing pulses such that the means for generating pacing pulses generates pacing pulses at the lower rate for a second predetermined time period before switching back to pulsing dependent on the control signal generated by the means for sensing physical activity.

4. A cardiac pacer according to claim 1, further comprising means for controlling said means for generating pacing pulses such that said means for generating pacing pulses generates pulses at the lower rate until the control signal falls below the predetermined high rate, whereupon the control signal resumes control of the pacing rate.

5. A cardiac pacer for pacing a heart in a patient comprising:
   means for generating pacing pulses at a predetermined pacing rate;
   means for transmitting the pacing pulses to the heart for pacing;
   means for sensing physical activity of said patient and for generating a control signal dependent thereon;
   a voltage to pulse rate converter to which the control signal is supplied;
   an analog signal to digital control word converter to which the output of the voltage to pulse rate converter is supplied;
   a time base register to which the output signal of the analog signal to digital control word converter is supplied;
   a decremental counter to which the output of said time base register is supplied which is set to higher zero counting speed when the activity rate increases;
   a zero decoder at the output of the decremental counter, said zero decoder being connected with and controlling means for generating pacing pulses such that a pacing pulse is generated at each zero count;
   means for monitoring when the pacing rate runs at least at a predetermined high rate for a predetermined time period and for generating an output signal if said high rate is reached; and
   means for forcing said pacing rate back to a lower rate dependent on said output signal.

6. A cardiac pacer as claimed in claim 5, wherein said means for forcing the pacing rate to a lower rate comprises a gate connected between the time base register and the analog signal to digital control word converter, said gate disconnecting the time base register from the analog signal to digital control word converter if the pacing rate runs at least at the predetermined high rate for the predetermined time period so that the time base register returns to the predetermined basic pacing rate.

7. A cardiac pacer as claimed in claim 6 wherein said means for forcing the pacing rate to a lower rate further comprises a high rate comparator for the output of the time base register, a high rate value generator for generating a predetermined high rate signal for comparison with the output of said time base register in said comparator, said high rate comparator controlling said gate dependent on the comparator output signal and the programmable time period such that the gate blocks the output of the analog signal to digital control word converter during said programmable time period.

8. A cardiac pacer as claimed in claim 7, wherein said means for forcing the pacing rate to a lower rate further comprises an integrator for the output of the high rate comparator, a threshold discriminator for the output of the integrator, said threshold discriminator having a threshold which can be varied according to the predetermined high rate time period, and a monostable multivibrator which is triggered by the threshold discriminator to close the gate when the output of the integrator exceeds the threshold.

9. A cardiac pacer as claimed in claim 8, further comprising means for preselecting the pulse width of the monostable multivibrator according to the programmable time period.

10. A method for pacing a heart in a patient comprising the steps of:
    generating pacing pulses at a predetermined basic pacing rate;
    transmitting the pacing pulses to the heart for pacing thereof;
    sensing physical activity of said patient and generating a control signal dependent thereon;
    varying the predetermined basic pacing rate dependent upon the control signal;
    monitoring when the pacing rate runs at least at a predetermined high rate for a predetermined time period and generating an output signal if said high rate is reached; and
    forcing said pacing rate back to a lower rate dependent on said output signal.

11. A method as claimed in claim 10, wherein the step of forcing the pacing rate back to a lower rate is further defined by forcing the pacing rate back to the predetermined basic pacing rate if the pacing rate runs at least at a predetermined high rate for a predetermined time period.

12. A method as claimed in claim 10, comprising the additional steps of:
    generating pacing pulses at said lower rate for a second predetermined time period; and
    thereafter switching back to generating pacing pulses dependent upon said control signal generated by said means for sensing physical activity.

13. A method as claimed in claim 10, comprising the additional steps of:
    generating pacing pulses at said lower rate until said control signal falls below said predetermined high rate; and
    thereafter resuming control of said pacing rate by said control signal.

14. A method for pacing a heart in a patient comprising the steps of:
    generating pacing pulses at a predetermined basic pacing rate;
    transmitting the pacing pulses to the heart for pacing thereof;
    sensing physical activity of said patient and generating a control signal dependent thereon;
    converting a voltage from said means for sensing physical activity into a pulse rate;
    converting said pulse rate into a digital control word;
    selecting a time base from a time base register based on said digital control word;
    using said time base to decrement a counter to zero, said time base selected according to said digital control word decrementing said counter at a faster rate as said sensed physical activity increases;

supplying said control signal to said means for generating pacing pulses for generating a pacing pulse each time said counter reaches zero, and simultaneously resetting said counter;

monitoring when the pacing rate runs at least at a predetermined high rate for a predetermined time period and generating an output signal if said high rate is reached; and forcing said pacing rate back to a lower rate dependent on said output signal.

15. A method as claimed in claim 14, wherein the step of forcing the pacing rate back to a lower rate is further defined by the steps of:

blocking transmittal of said digital control word to said time base register by a logic gate if the pacing rate runs at or above said predetermined high rate for said predetermined time period; and supplying a time base from said time register when said time register is in a blocked condition which corresponds to said basic pacing rate.

16. A method as claimed in claim 15, wherein the step of forcing the pacing rate to a lower rate is further defined by the steps of:

comparing the output of said time base register with a predetermined rate value; and controlling blocking of said time base register by said gate based on the result of said comparison.

17. A method as claimed in claim 16, wherein the step of forcing the pacing rate to a lower rate is further defined by the steps of:

integrating the output of said comparator;

setting a selected threshold for the output of said integrator; and triggering a monostable multivibrator to switch said logic gate to a blocking condition when said threshold is exceeded by the output of said integrator.

* * * * *